United States Patent

Modglin

[11] Patent Number: 5,853,378
[45] Date of Patent: Dec. 29, 1998

[54] LUMBO-SACRAL ORTHOSIS

[76] Inventor: Michael D. Modglin, 203 Reisling Dr., Braselton, Ga. 30517

[21] Appl. No.: 942,745
[22] Filed: Oct. 2, 1997
[51] Int. Cl.⁶ ...................................................... A61F 5/00
[52] U.S. Cl. .......................................... 602/19; 128/100.1
[58] Field of Search ............................. 602/19; 128/96.1, 128/99.1, 100.1

[56] References Cited

U.S. PATENT DOCUMENTS

| | | |
|---|---|---|
| 2,100,964 | 11/1937 | Kendrick . |
| 3,926,183 | 12/1975 | Spiro . |
| 3,927,665 | 12/1975 | Wax . |
| 4,099,524 | 7/1978 | Cueman et al. ............................ 602/19 |
| 4,175,553 | 11/1979 | Rosenberg . |
| 4,459,979 | 7/1984 | Lewis, Jr. . |
| 4,475,543 | 10/1984 | Brooks et al. . |
| 4,508,110 | 4/1985 | Modglin . |
| 4,559,933 | 12/1985 | Batard et al. . |
| 5,074,288 | 12/1991 | Miller . |
| 5,188,585 | 2/1993 | Peters ....................................... 602/19 |
| 5,241,704 | 9/1993 | Sydor .................................... 602/19 X |
| 5,259,831 | 11/1993 | LeBron ................................. 602/19 X |
| 5,267,948 | 12/1993 | Elliott ....................................... 602/19 |
| 5,302,171 | 4/1994 | Pearson et al ............................ 602/19 |
| 5,362,304 | 11/1994 | Varn ......................................... 602/19 |
| 5,399,151 | 3/1995 | Smith ....................................... 602/19 |
| 5,499,965 | 3/1996 | Sanchez ................................... 602/19 |
| 5,560,046 | 10/1996 | Iwamasa et al. ...................... 602/19 X |
| 5,632,723 | 5/1997 | Grim ........................................ 602/19 |
| 5,634,891 | 6/1997 | Beczak Sr. et al. ..................... 602/19 |
| 5,656,020 | 8/1997 | Greengarg ................................ 602/19 |
| 5,693,006 | 12/1997 | Slautterback ............................. 602/19 |
| 5,722,940 | 3/1998 | Gaylord Jr. et al. .................... 602/19 |

Primary Examiner—Linda C.M. Dvorak
Attorney, Agent, or Firm—William M. Hobby, III

[57] ABSTRACT

A lumbo-sacral orthopedic brace apparatus is formed of flexible materials to fit over a patient's torso and has a front flexible section shaped to fit over the front of a patient's torso and covered with a hook and loop fastener loop material. A plurality of flexible straps are attached to the brace front section on either side thereof by being attached to a hook and loop fastener hook strap which is attached to the brace front section loop material. A rear flexible section is shaped to fit over the rear of a patient's torso and has a plurality of loops attached to each side thereof by being attached to a hook and loop hook strap which is attached to the brace rear section loop material. The hook straps are able to be attached to the front or to the back at any angle at any point across the entire front or back, respectively, rapidly altering the orthosis to accommodate a broad range of figure types. The straps on the front flexible section are looped through the loops on the rear section and are connected in groups to common flexible straps. Pulling one common strap pulls a plurality of straps through the loops. Each common strap has hook material attached thereto so that the common strap can be attached to the front section loop material in different positions and angles to adjust the stress of the rear flexible member on the rear of a patient's torso.

16 Claims, 3 Drawing Sheets

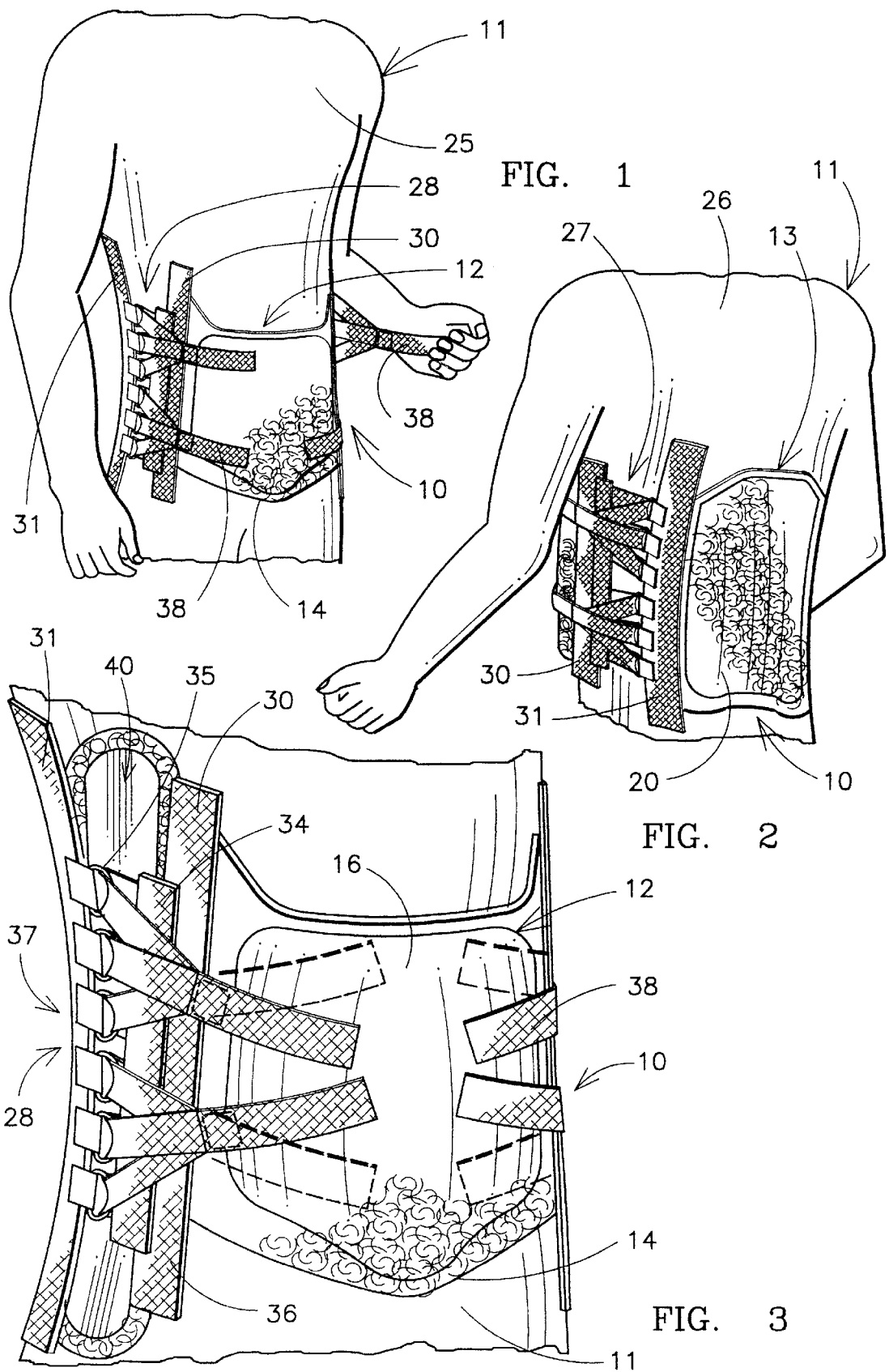

LUMBO-SACRAL ORTHOSIS

BACKGROUND OF THE INVENTION

The present invention relates to an orthopedic brace and especially to a soft flexible orthopedic brace providing for multiple and rapid adjustment.

Although body jackets have been known and used for many years in the treatment and rehabilitation of the spine, elderly, injured, and handicapped persons have experienced difficulty in putting on rigid and soft flexible orthoses and generally require assistance. It is known to use corset lacings and corset buckles in combination with soft, flexible orthoses to provide even adjustment and an easy release. For example, the buckle taught by Camp in U.S. Pat No. 2,053,600 has improved the adjustment of nonrigid orthoses. Using the Camp buckle, corset lacings threaded through the buckle are adjusted with the orthosis on the patient. The buckle straps are attached to the orthosis with snaps, permitting ease of removal and reinstallation.

In the past, rigid orthoses have used corset lacing on one side to secure the anterior section to the posterior section and once adjusted, remains permanently fixed. The other side may be attached by two straps, resulting in a body jacket that is difficult to put on. When the straps are tightened, the opposing side may rotate or twist toward the last adjusted strap. For many patients, this design requires two people to properly position the orthosis. Thus, many elderly and handicapped patients are unable to don the jacket.

A rigid body jacket is also shown in U.S. Pat. No. 4,202,327 having a number of straps for connecting right and left sections with the straps secured to the jacket with hook and loop strips. The necessity for adjusting straps both front and rear prevents use by many patients without assistance in doffing and donning the orthosis.

In my prior U.S. Pat. No. 4,508,110, a body jacket-type orthoses limits motion in thoracic or lumbo-sacral areas and uses a rigid orthoses design for ease of adjustment by a patient and which can be adjusted by the patient by pulling on a plurality of laces, each attached to a short strap having VELCRO thereon which is used to attach the straps to predetermined positions on the rigid brace members.

Other prior art U.S. patents for orthoses can be seen in the Brooks et al. U.S. Pat. No. 4,475,543, for a lumbo-sacral brace using an elastic belt fastened with a pouch in combination with a semi-wrap-around polyurethane foam splint cured in place in the pouch. In the Kendrick U.S. Pat. No. 2,100,964, a surgical belt is illustrated in which a plurality of laces are interconnected to a single strap on either side thereof. In the Spiro U.S. Pat. No. 3,926,183, a dorsal lumbo sacral support combines elastic and non-elastic straps in a support device for a person's back, thoracic or pelvic areas. The Wax U.S. Pat. No. 3,927,665, is for a lumbo-sacral support having an elastic body encircling band and inelastic tensioning system. The Miller U.S. Pat. No. 5,074,288, illustrates a soft body brace attached to a patient with a plurality of straps. The Saunders patent is a back support system with interchangeable and positionally adjustable orthotic support. The Rosenberg U.S. Pat. No. 4,175,553, is also a lumbo-sacral orthosis orthopedic support for encircling the torso and has a plurality of straps. The Lewis, Jr. U.S. Pat. No. 4,459,979 is an orthopedic appliance made of resilient material conforming to the lower back of a person and uses a plurality of adjustable straps. The Varn U.S. Pat. No. 5,362,304 is a thoracic lumbar sacral orthosis device formed as a jacket and has support plates which can attach thereto. The Peters U.S. Pat. No. 5,188,585 is a lumbo-sacral orthopedic support which encircles the torso of a patient and has adjustable strap portions. The Batard et al. U.S. Pat. No. 4,559,933, is an orthopedic lumbo-sacral corset using semi-rigid elements and inflatable pads.

There is a need for a soft flexible glove-like body jacket orthosis which can be adjusted on the patient and then easily removed and replaced by the patient.

The present invention is directed towards a flexible lumbo-sacral orthopedic brace which fits in a glove-like fashion and can be easily attached and tightened in a wide variety of positions for a wide variety of body shapes and provides for optional side splints and lightweight splints removably attachable thereto.

SUMMARY OF THE INVENTION

A lumbo-sacral orthopedic brace apparatus is formed of flexible materials to fit over a patient's torso and has a front flexible section shaped to fit over the front of a patient's torso having one side having all or a portion thereof covered with a loop type material. A plurality of flexible straps are attached to the brace front section on either side thereof by being attached to a VELCRO hook and loop material hook strap which is attached to the brace front section VELCRO loop material. A rear flexible section is shaped to fit over the rear of a patient's torso and has a plurality of loops attached to each side thereof by being attached to a VELCRO hook and loop material hook strap which is attached to the brace rear section VELCRO hook and loop loop material. These VELCRO hook and loop hook straps are able to be attached to the front or to the back at any angle at any point across the entire front or back respectively rapidly altering the orthosis to accommodate a broad range of figure types. Additionally, these VELCRO hook and loop hook straps allow raising of or lowering of the front or back sections in relation to one another. The straps on either side of the front flexible section are individually looped through the loops on the rear section and are connected in groups to common flexible straps so that pulling one common flexible strap pulls a plurality of flexible straps through the loops. Each common strap has a portion of VELCRO hook and loop material hook material attached thereto so that the common strap can be attached to the front section VELCRO hook and loop loop material in different positions and angles to adjust the stress of the rear flexible member on the rear of a patient's torso. Both the front flexible section and the rear flexible section have pockets therein for lightweight rigid splint members shaped to fit into each pocket. Each also being made of VELCRO hook and loop loop material. Each splint member has a plurality of openings therein to reduce the weight. One or two side splints have a pair of loops thereon for passing the top middle and bottom middle straps therethrough so that the side splints can be pulled tight against the side of the patient.

The side splint padding as well as the front and rear sections can be made of a VELCRO hook and loop loop foam laminate material. The side splints themselves as well as the front and rear splints are made of a lightweight rigid plastic, such as but not limited to high density polyethylene.

BRIEF DESCRIPTION OF THE DRAWINGS

Other objects, features, and advantages of the present invention will be apparent from the written description and the drawings in which:

FIG. 1 is a perspective view of a lumbo-sacral orthopedic brace being attached to a patient's torso;

FIG. 2 is a rear perspective of the attached orthopedic brace in accordance with FIG. 1;

FIG. 3 is a partial front perspective of the orthopedic brace of FIGS. 1 and 2 having the splint attachment;

DETAILED DESCRIPTION OF THE PREFERRED EMBODIMENT

Figure 4:
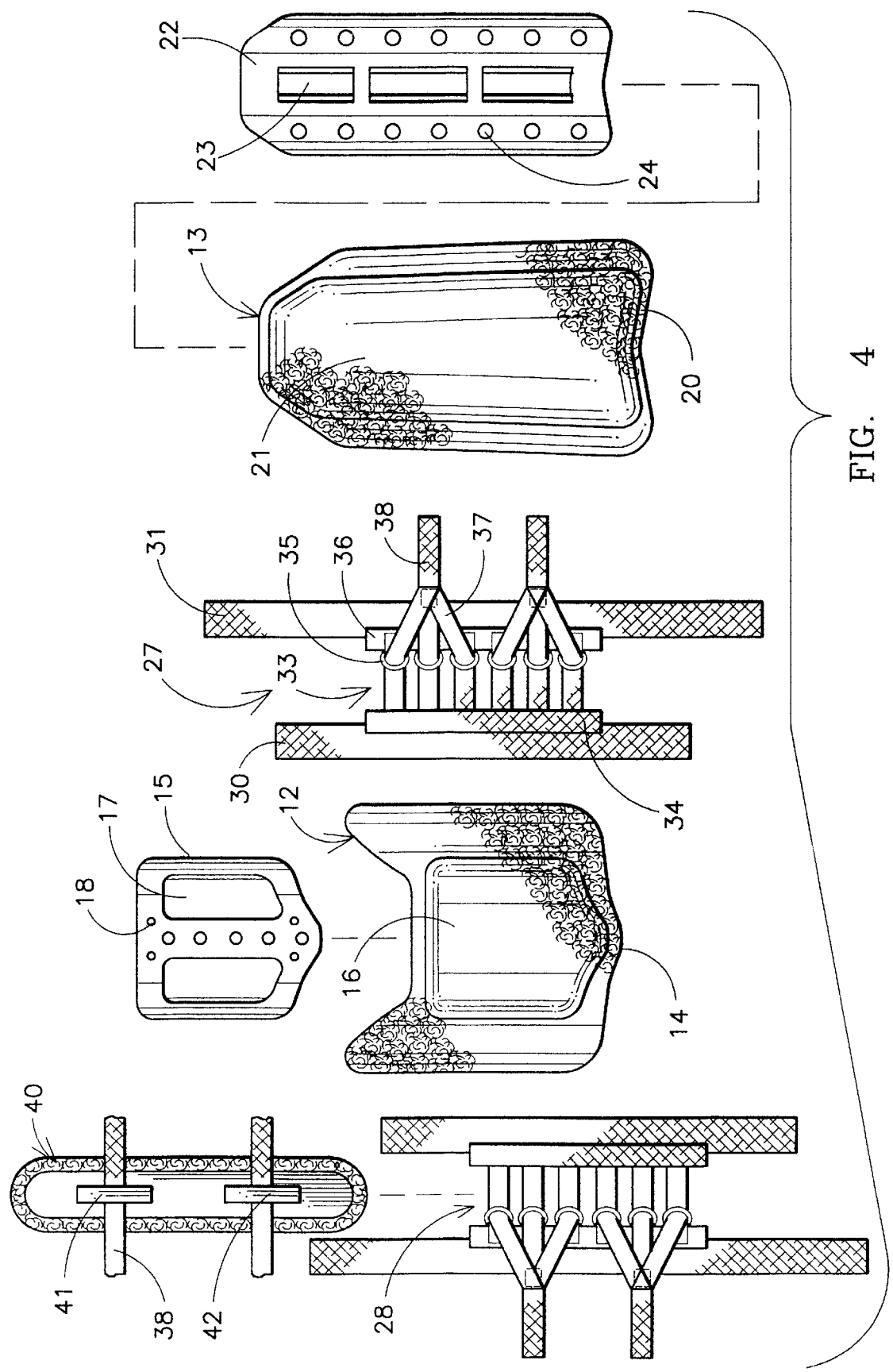
FIG. 4 is an exploded sectional view of an orthopedic brace in accordance with the present invention.

Referring to the drawings of FIGS. 1–7, a lumbo-sacral orthopedic brace 10 is used for limiting or controlling the motion in a thoracic and lumbo-sacral areas of the spine of a patient 11. The orthoses 10 is a more anatomically correct type of orthoses made of a soft breathable material with strategically placed splints as well as adjustable shape controls 27 and 28 which act to simulate the lateral obliques as well as act to provide form fit to an endless variety of figure types. The orthoses 10 is a flexible glove-like orthosis which can be adjusted for any patient and includes a soft flexible front section 12 and a soft flexible rear section 13. The front section 12 has a front surface formed of one portion of a hook and loop material 14 and, more specifically, the loop material is generally used on section 12. A lightweight polymer splint 15 is shaped to fit into a pocket 16 on the front of front section 12. The splint or brace member 15 has openings or removed portions 17 therein along with a plurality of smaller openings 18 which reduce the weight of the splint portion inserted in the pocket 16. Similarly, the flexible rear section 13 has a covering of a hook and loop material 20 on the surface thereof which may also be the loop portion of the hook and loop material. A pocket 21 is shaped to receive the shaped polymer splint or brace member 22 which also has removed portions or openings 23 therethrough as well as smaller openings 24.

The front and rear brace sections 12 and 13 are connected to the front 25 and rear 26 of the patient 11 with set connection straps 27 and 28 on each side thereof. Each connection has a hook and loop loop front hook strip 30 which connects to the hook and loop loop material 14 of the flexible front section 12 of the brace 10. A second length of hook material 31 attaches to the hook and loop material loop surface 20 of the flexible rear brace section 13. The front brace section has a plurality of straps 33 which are attached to the hook strip 30 with a nylon strip 34. Each strap 33 is passed through a loop 35 which is attached to a nylon strip 36 attached to the hook strap 31 so that each loop 35 is all held to the soft flexible rear section 13 while the straps are held to the hook and loop hook strip 30 which is attached to the flexible front section 12. Each group of three straps 37 are attached to a common strap 38 which is made of a VELCRO hook and loop hook material attached thereto. Each attaching assembly 27 and 28 is illustrated having two sets of three straps 33 attached to each common strap 38 so that pulling on one common strap 38 pulls the three straps. In this configuration, four common straps 38 are pulled to selectively pull the twelve different straps and may be pulled straight or at any angle desired to form-fit the front and rear brace sections 12 and 13 to a patient's torso. The straps 38 are pulled back over the soft flexible front section 12 and attached at any angle or position desired to the hook and loop loop cover 14, as illustrated in FIGS. 1 and 3. Additionally, the hook strips 30 and 31 of assemblies 27 and 28 can also be attached at any angle anywhere across the front or back. In FIGS. 5 to 7, only one hook strip is shown attached to the front and to the back and shows other alternatives connections in order to fit the various figure types shown.

This arrangement allows for a very flexible orthoses for fitting any patient and for applying pressure in any manner desired for a particular patient, as seen in FIGS. 3 and with the dashed lines. The common straps can be attached in a wide variety of different angles to pull on the straps 33 in different degrees for applying different forces to the front and rear sections of the orthosis. Both splint members 15 and 22 can be inserted or removed as desired for a particular patient. A pair of side splints 40 are also provided and have a pair of loops 41 and 42 thereon which allows the insertion of the middle top and middle bottom strap members 33 therethrough so that the side splints can be positioned on the side of a patient, as illustrated in FIG. 3.

The flexible front panels 13 and 12 as well as the padding for side splints 40 can be made of a soft breathable material, such as an ORTHO-WICK laminated to a foam with a loop material outer layer covered polymer foam to provide a breathable material which is cool and flexible and fits onto the patient in a glove-like manner which can be adjusted to form a soft body jacket readily adjusted and readjusted to apply the forces desired for a particular patient. The splint members 15, 22 and 40 can be made of a high density polyethylene material or any substantially rigid or semi-rigid polymer material desired but can be made of a metal or any other material without departing from the spirit and scope of the invention.

Figure 5A:
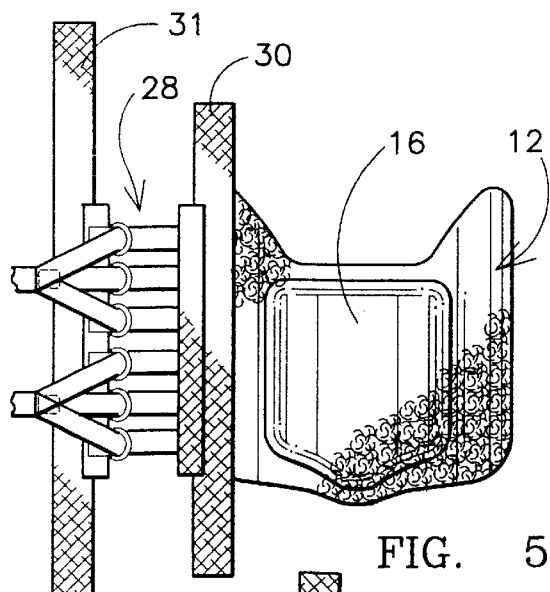
FIGS. 5A and 5B shows the orthosis of FIGS. 1–4 adjusted to fit a straight figured person.
Figure 6A:
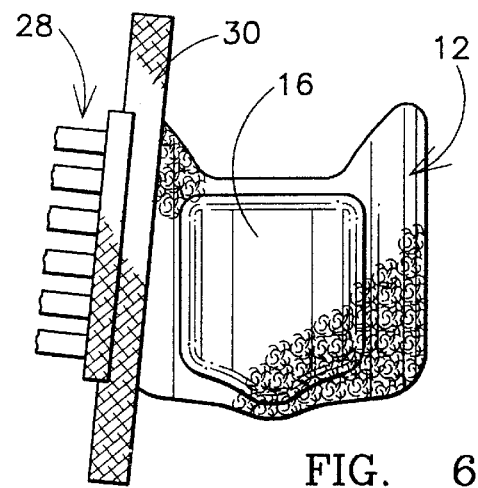
FIGS. 6A and 6B shows the orthosis of FIGS. 1–4 adjusted to fit an average figured person.
Figure 5B:
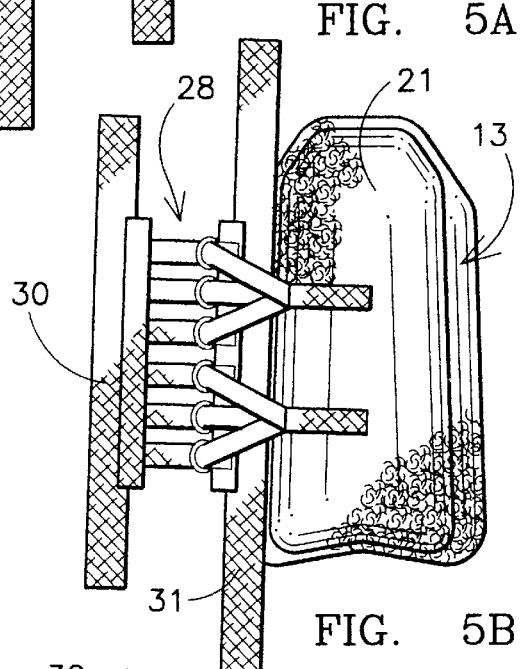
Figure 6B:
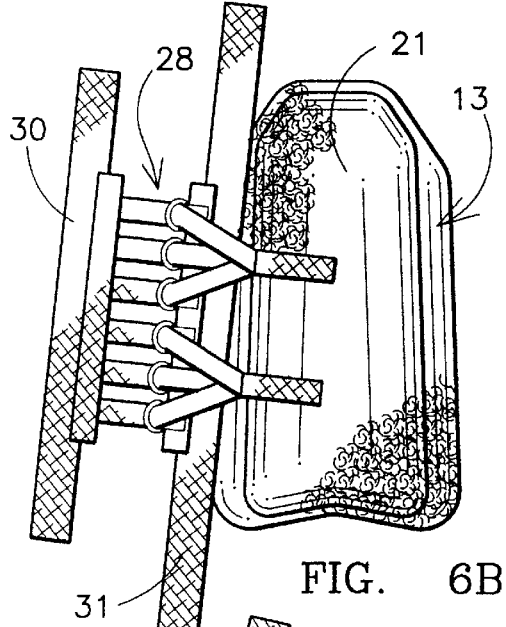
Figure 7A:
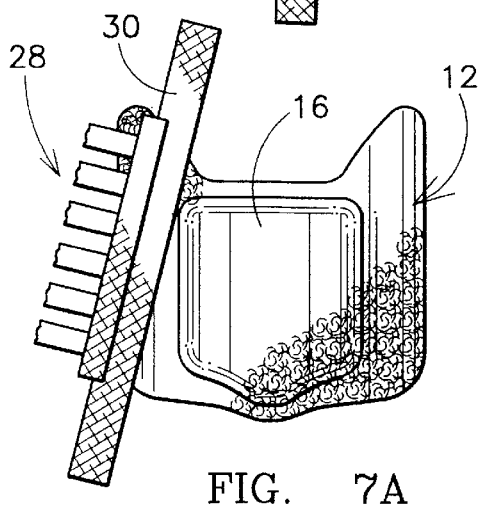
FIGS. 7A and 7B shows the orthosis of FIGS. 1–4 adjusted to fit a full figured person.
Figure 7B:
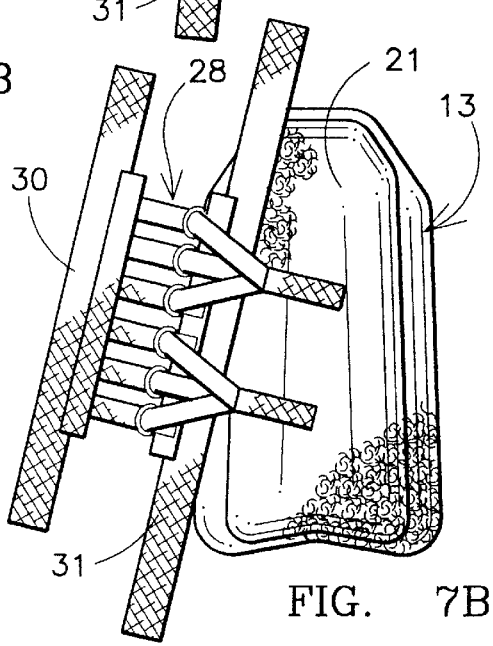

FIGS. 5A and 5B illustrates the present orthosis 10 adjusted for a patient having a straight figure of hip to waist dimensions. FIGS. 6A and 6B illustrate the adjustments for a patient having an average figure of hip to waist dimensions and FIGS. 7A and 7B illustrates the adjustments for a patent having a full figure of hip to waist dimensions.

The orthosis 10 is made to simulate the viscoelastic qualities of the human body while combining the best features of a soft corset with those of a rigid plastic body jacket and to form-fit the orthoses to the patient to lock-out certain motions of the spine and yet provide a comfort level suitable for long term wear. The orthosis can be custom fitted to different types of patients, including scoliosis patients, without alterations and modifications requiring a sewing machine and/or grinder and can be worn long term by wheelchair bound patients without having to make a custom cast and preventing the dangers of skin break-down. The brace is also lightweight and vertically fits patients with straight figures, full figure types, and average figures. However, the present invention should not be considered limited to the forms shown which are to be considered illustrative rather than restrictive.

I claim:

1. A lumbo-sacral orthopedic brace comprising:

a front flexible member shaped to fit over the front of a patient's torso and having front and rear sides and having first and second edge portions, said front side having the surface thereof formed of hook and loop loop material;

a rear flexible member shaped to fit over the rear of a patient's torso and having first and second edge portions;

a first plurality of flexible straps attached to said front flexible member first edge portion;

a second plurality of flexible straps attached to said front flexible member second edge portion;

a first plurality of loops attached to said rear flexible member first edge portion and having each one of said first plurality of flexible straps passing through one of said first plurality of loops and a plurality of said first straps being attached to one common flexible strap having one portion of hook and loop hook material attached thereto and a second plurality of said first straps being attached to a second common flexible strap having one portion of hook and loop hook material attached thereto; and a second plurality of loops attached to said rear flexible member second edge portion and having each one of said second plurality of flexible straps passing through one of said second plurality of loops and a plurality of said second straps being attached to one common flexible strap having one portion of hook and loop hook material attached thereto and a second plurality of said second straps being attached to a second common flexible strap having one portion of hook and loop hook material attached thereto, whereby each said common strap can pull a plurality of straps through a plurality of loops and be attached to said front flexible member hook and loop loop material at any desired position for adjusting the brace on a patient.

2. A lumbo-sacral orthopedic brace in accordance with claim 1 in which said first and second plurality of flexible straps are each attached to a strip of hook and loop hook material which is removably attached to said front flexible member of hook and loop loop material.

3. A lumbo-sacral orthopedic brace in accordance with claim 1 in which said first and second plurality of loops are each attached to a strip of hook material which is removably attached to said rear flexible member of hook and loop loop material.

4. A lumbo-sacral orthopedic brace in accordance with claim 1 in which said front flexible member has pocket formed therein.

5. A lumbo-sacral orthopedic brace in accordance with claim 4 including a substantially rigid splint member shaped to fit over front torso and sized to fit in said front flexible member pocket and having an open area therein.

6. A lumbo-sacral orthopedic brace in accordance with claim 5 in which said substantially rigid splint member has a plurality of openings therein.

7. A lumbo-sacral orthopedic brace in accordance with claim 6 in which said substantially rigid splint member is made of a polymer material.

8. A lumbo-sacral orthopedic brace in accordance with claim 1 in which said rear flexible member has a pocket formed therein of hook and loop loop material.

9. A lumbo-sacral orthopedic brace in accordance with claim 8 including a substantially rigid splint shaped to fit over the rear torso area and having an open area therein.

10. A lumbo-sacral orthopedic brace in accordance with claim 9 in which said rear splint has a plurality of open areas therein.

11. A lumbo-sacral orthopedic brace in accordance with claim 10 in which said substantially rigid splint is made of a polymer material.

12. A lumbo-sacral orthopedic brace in accordance with claim 1 including a side splint having a plurality of loops formed thereon for said straps to pass through to thereby mount a side splint on one side of a patient's torso.

13. A lumbo-sacral orthopedic brace in accordance with claim 12 including two side splints, one for each side of a patient's torso.

14. A lumbo-sacral orthopedic brace in accordance with claim 13 in which each said side splint is made of a substantially rigid polymer material padded with a breathable foam laminate.

15. A lumbo-sacral orthopedic brace in accordance with claim 1 in which said front flexible member is a hook and loop foam laminate.

16. A lumbo-sacral orthopedic brace in accordance with claim 15 in which said rear flexible member is a hook and loop loop foam laminate.

* * * * *

UNITED STATES PATENT AND TRADEMARK OFFICE
CERTIFICATE OF CORRECTION

PATENT NO. : 5,853,378
DATED : December 19, 1998
INVENTOR(S) : Michael D. Modglin It is certified that error appears in the above-identified patent and that said Letters Patent is hereby corrected as shown below:

Column 5,
Line 36, after "has" and before "pocket" insert -- a --

Column 6,
Line 1, after "over" and before "front" insert -- the --
Line 1, after "front" and before "torso" insert -- of a patient's --
Line 14, after "rear" and before "torso" insert -- of a patient's --
Line 14, delete "area" after "torso" and before "and having"

Signed and Sealed this

Twenty-second Day of February, 2005

JON W. DUDAS
*Director of the United States Patent and Trademark Office*